(12) United States Patent
Yoshikawa

(10) Patent No.: US 11,751,840 B2
(45) Date of Patent: Sep. 12, 2023

(54) ULTRASONIC IMAGING DEVICE AND ULTRASONIC SIGNAL PROCESSING DEVICE

(71) Applicant: Hitachi, Ltd., Tokyo (JP)

(72) Inventor: Hideki Yoshikawa, Tokyo (JP)

(73) Assignee: FUJIFILM Healthcare Corporation, Kashiwa (JP)

(*) Notice: Subject to any disclaimer, the term of this patent is extended or adjusted under 35 U.S.C. 154(b) by 643 days.

(21) Appl. No.: 16/898,079

(22) Filed: Jun. 10, 2020

(65) Prior Publication Data

US 2021/0022702 A1    Jan. 28, 2021

(30) Foreign Application Priority Data

Jul. 26, 2019   (JP) .................................. 2019-137933

(51) Int. Cl.
    *A61B 8/06*    (2006.01)
    *A61B 8/02*    (2006.01)
    (Continued)

(52) U.S. Cl.
CPC .................. *A61B 8/06* (2013.01); *A61B 8/02* (2013.01); *A61B 8/463* (2013.01); *A61B 8/485* (2013.01); *A61B 8/488* (2013.01); *A61B 8/5276* (2013.01)

(58) Field of Classification Search
CPC .. A61B 8/06; A61B 8/02; A61B 8/463; A61B 8/485; A61B 8/488; A61B 8/5276;
(Continued)

(56) References Cited

U.S. PATENT DOCUMENTS

2008/0015440 A1* 1/2008 Shandas ................... A61B 8/13
    600/458
2010/0191111 A1    7/2010 Azuma
(Continued)

FOREIGN PATENT DOCUMENTS

JP    2006-55493 A    3/2006
JP    2013-544615 A    12/2013
(Continued)

OTHER PUBLICATIONS

Jensen JA, Nikolov SI, Yu AC, Garcia D. Ultrasound Vector Flow Imaging-Part I: Sequential Systems. IEEE Trans Ultrason Ferroelectr Freq Control. Nov. 2016;63(11):1704-1721. doi: 10.1109/TUFFC.2016.2600763. PMID: 27824555.*
(Continued)

*Primary Examiner* — Bo Joseph Peng
(74) *Attorney, Agent, or Firm* — Crowell & Moring LLP

(57) ABSTRACT

The present invention aims to obtain and provide one or more types of information desired by an operator with a high efficiency. From a probe that transmits an ultrasonic wave to a subject and receives the ultrasonic wave coming from the subject due to the transmission, a reception signal is received and the reception signal is processed. Accordingly, a movement vector indicating a movement amount and a movement direction is calculated and a movement vector distribution is determined for a plurality of points set at least two-dimensionally in the subject. A distribution of one or more desired movement vector components is extracted from the movement vector distribution.

12 Claims, 16 Drawing Sheets

(51) Int. Cl.
*A61B 8/00* (2006.01)
*A61B 8/08* (2006.01)

(58) Field of Classification Search
CPC ....... A61B 8/54; A61B 8/5223; A61B 8/5207; A61B 8/085; A61B 8/08; G01S 7/52036; G01S 15/8977; G01S 15/8984; G01S 7/52042
See application file for complete search history.

(56) References Cited

U.S. PATENT DOCUMENTS

| | | |
|---|---|---|
| 2012/0283567 A1 | 11/2012 | Chono |
| 2020/0060655 A1 | 2/2020 | Fraser et al. |

FOREIGN PATENT DOCUMENTS

| | | |
|---|---|---|
| JP | 5411699 B2 | 2/2014 |
| JP | 5753798 B2 | 7/2015 |
| JP | 2015-186491 A | 10/2015 |
| JP | 2015-198710 A | 11/2015 |
| JP | 2019-88672 A | 6/2019 |
| WO | WO 2007/063619 A1 | 6/2007 |
| WO | WO 2011/096556 A1 | 8/2011 |

OTHER PUBLICATIONS

Voorneveld et al., "High Frame Rate Ultrasound Particle Image Velocimetry for Estimating High Velocity Flow Patterns in the Left Ventricle," IEEE Transactions on Ultrasonics, Ferroelectrics, and Frequency Control, Dec. 2018, pp. 2222-2232, vol. 65, No. 12 (11 pages).

Yiu et al., "Vector Projectile Imaging: Time-Resolved Dynamic Visualization of Complex Flow Patterns," Ultrasound in Medicine and Biology, 2014, pp. 2295-2309, vol. 40, No. 9 (15 pages).

Yu et al., "Eigen-Based Clutter Filter Design for Ultrasound Color Flow Imaging: A Review," IEEE Transactions on Ultrasonics, Ferroelectrics, and Frequency Control, May 2010, pp. 1096-1111, vol. 57, No. 5 (16 pages).

Japanese-language Office Action issued in Japanese Application No. 2019-137933 dated Mar. 14, 2023 with English translation (eight (8) pages).

\* cited by examiner

[FIG. 1]
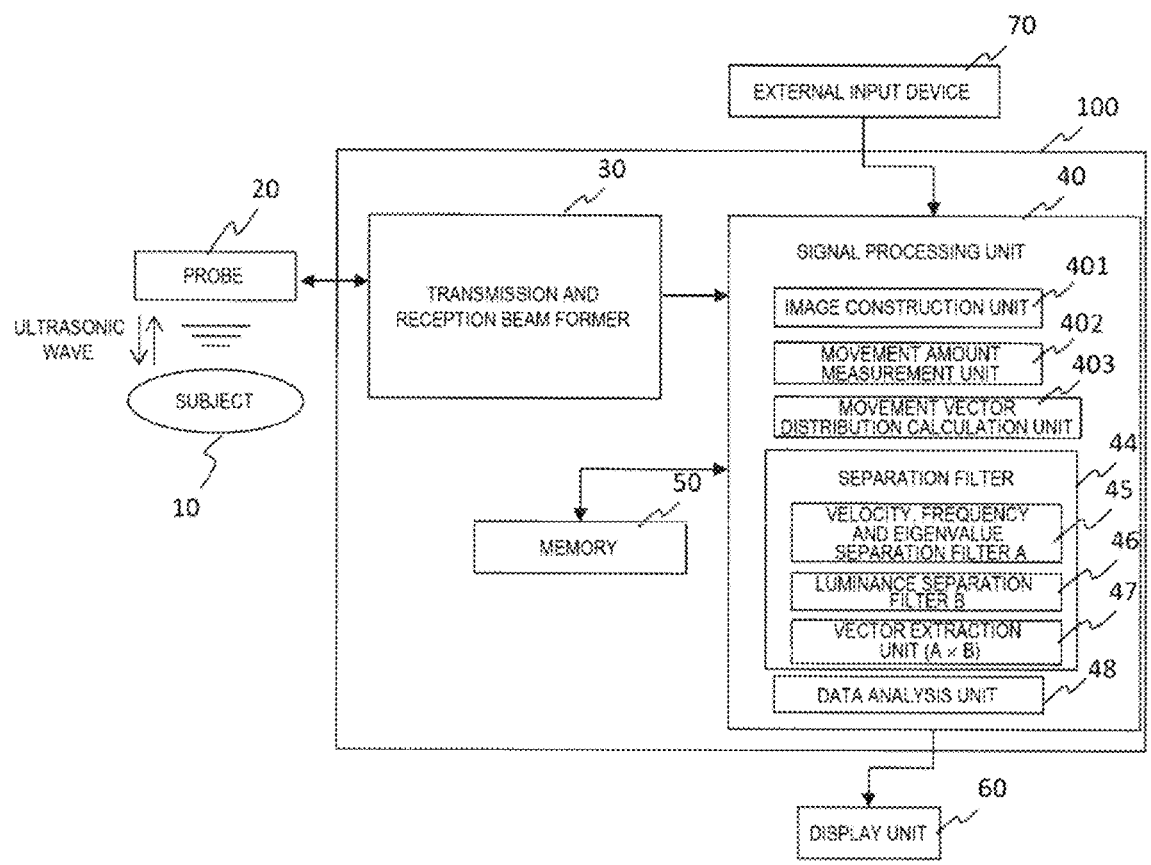

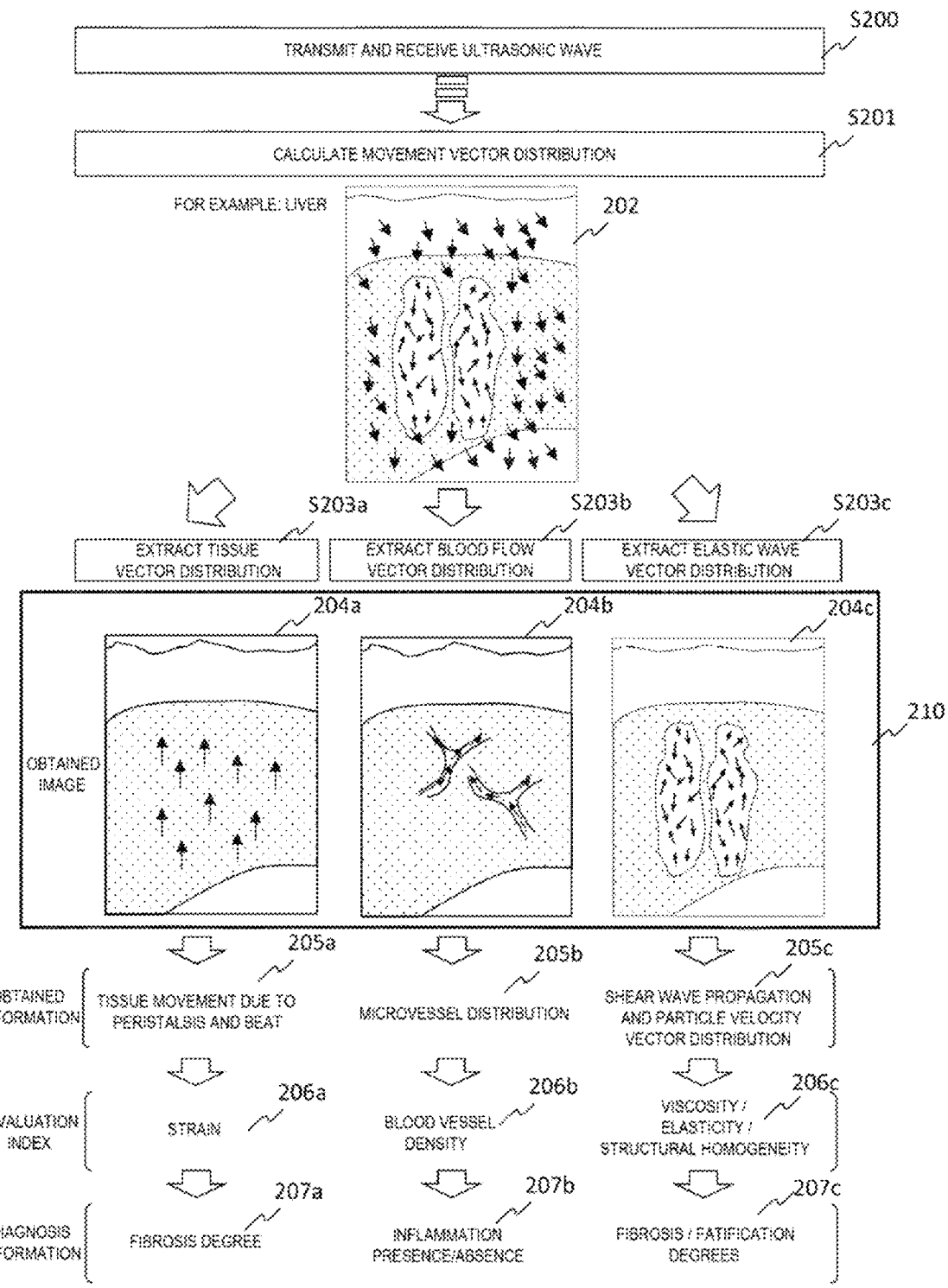

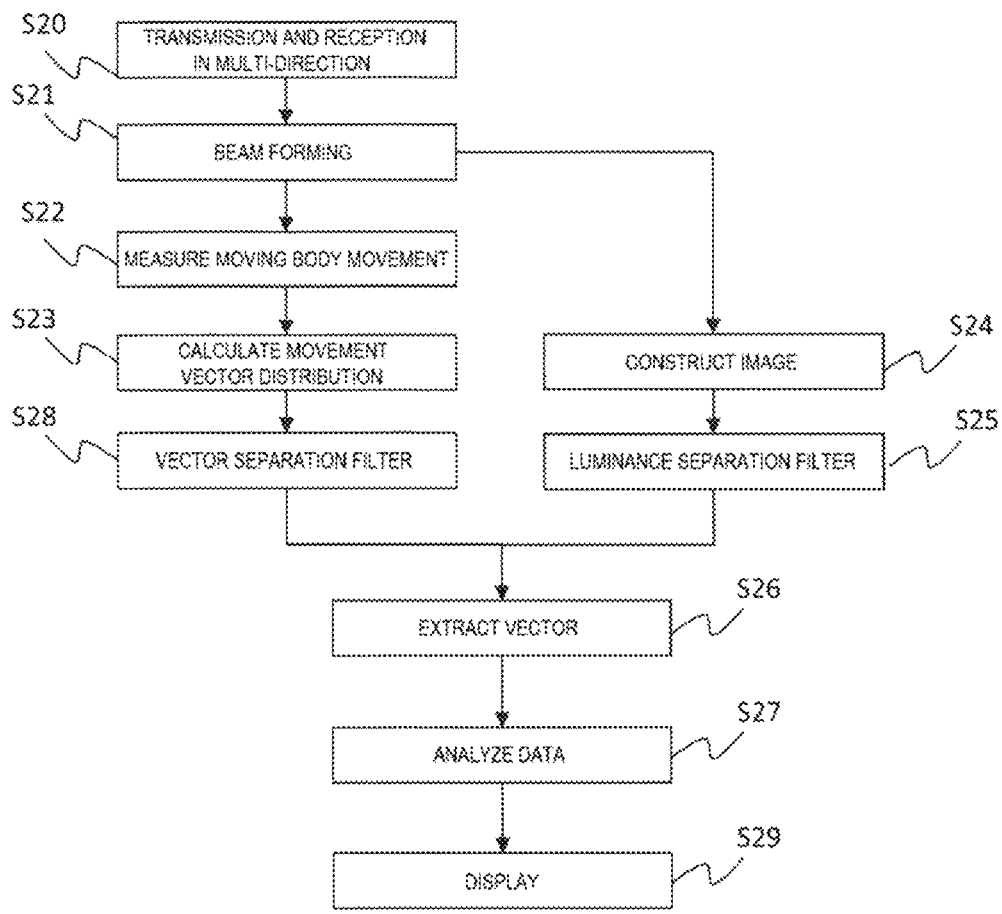

[FIG. 7]
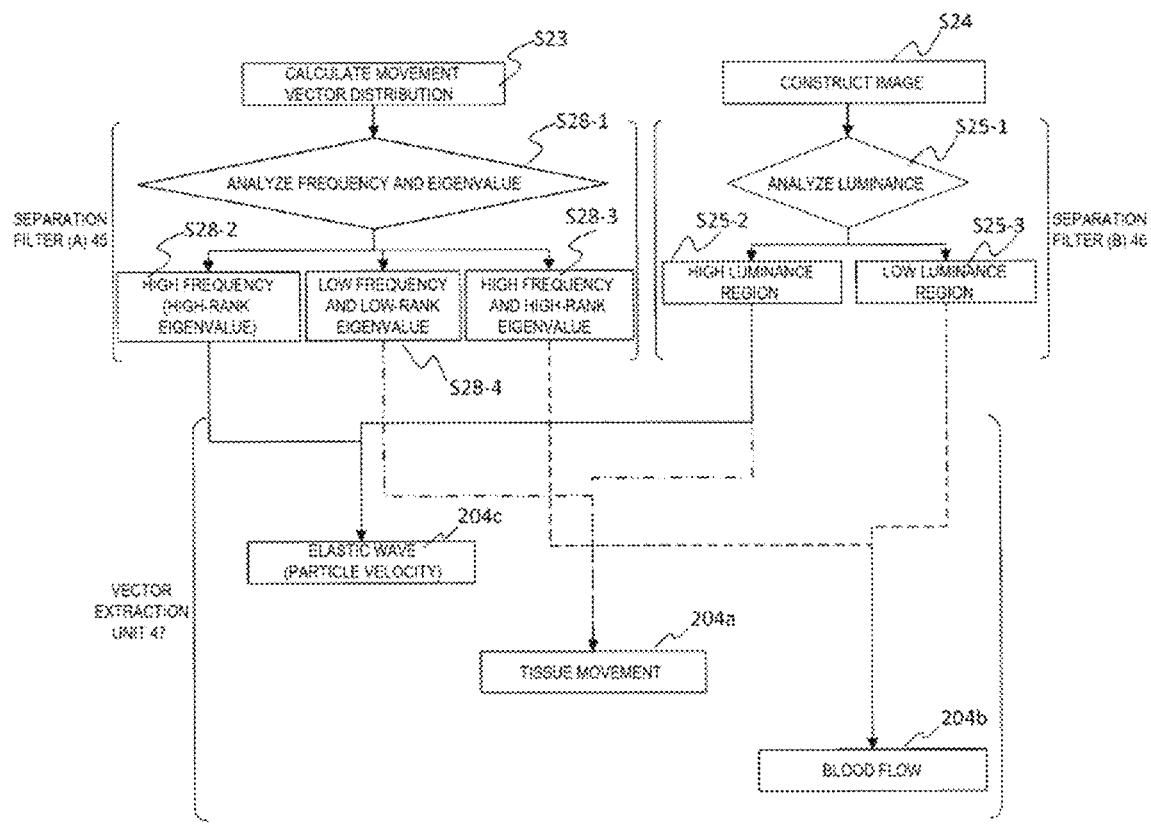
[FIG. 8]
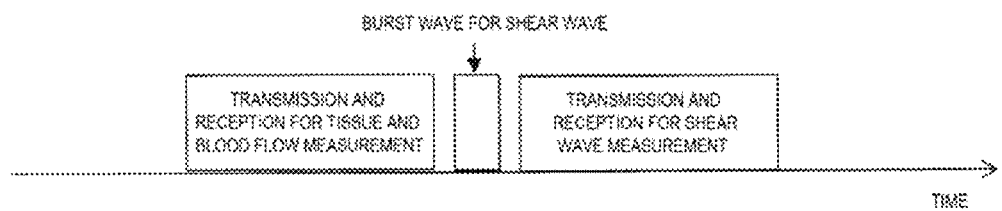

FIG. 10A

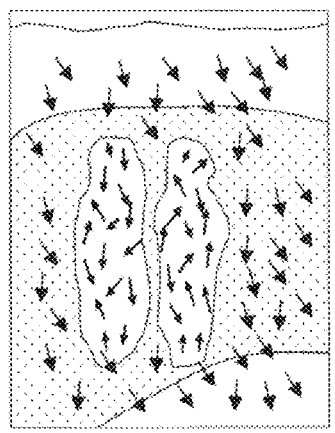

VECTOR SEPARATION FILTER

FIG. 10B

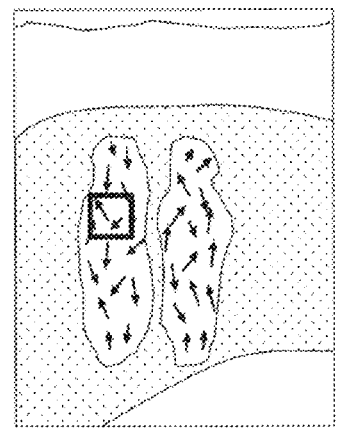

EXTRACT VECTOR IN REGION

FIG. 10C $$\begin{bmatrix} v_{11} & \cdots & v_{1M} \\ \vdots & \ddots & \vdots \\ v_{N1} & \cdots & v_{NM} \end{bmatrix}$$

$$v_{nm} = r_{nm} e^{-i\theta_{nm}}$$

REPRESENTATION OF VECTOR IN COORDINATE (n, m), WHERE r SHOWS VECTOR MAGNITUDE, θ SHOWS ANGLE, AND (N, M) SHOWS MATRIX SIZE OF SPECIFIED REGION.

FIG. 10D $$\sigma^2 = \frac{1}{NM} \sum_{n,m}^{N,M} (\theta_{nm} - \overline{\theta_{nm}})^2$$

σ: VARIANCE OF ANGLE

FIG. 14A
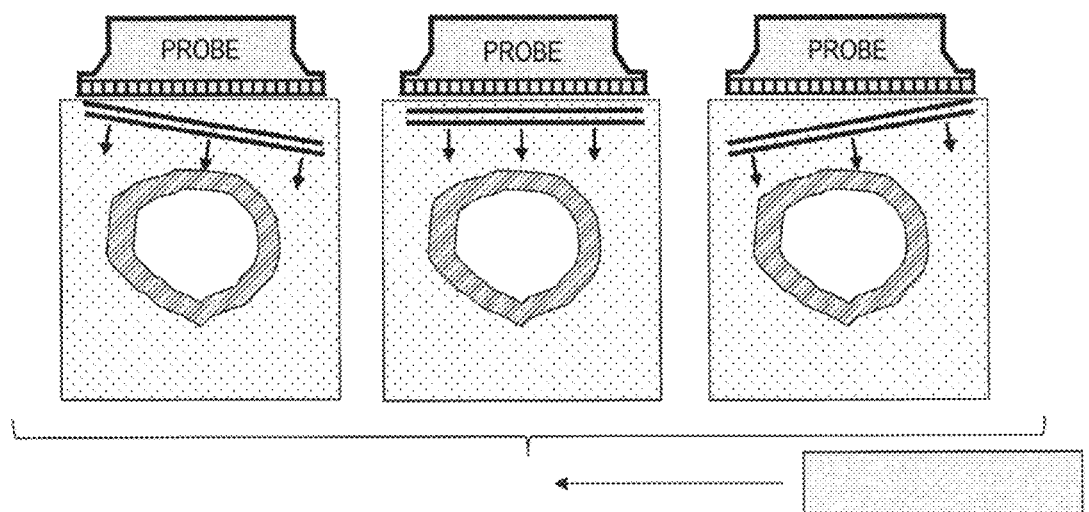
FIG. 14B
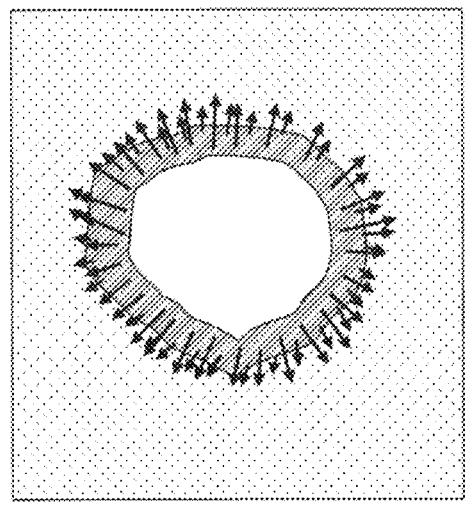
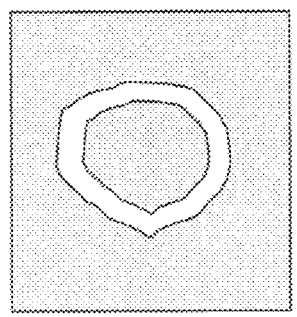
FIG. 14C

[FIG. 16]
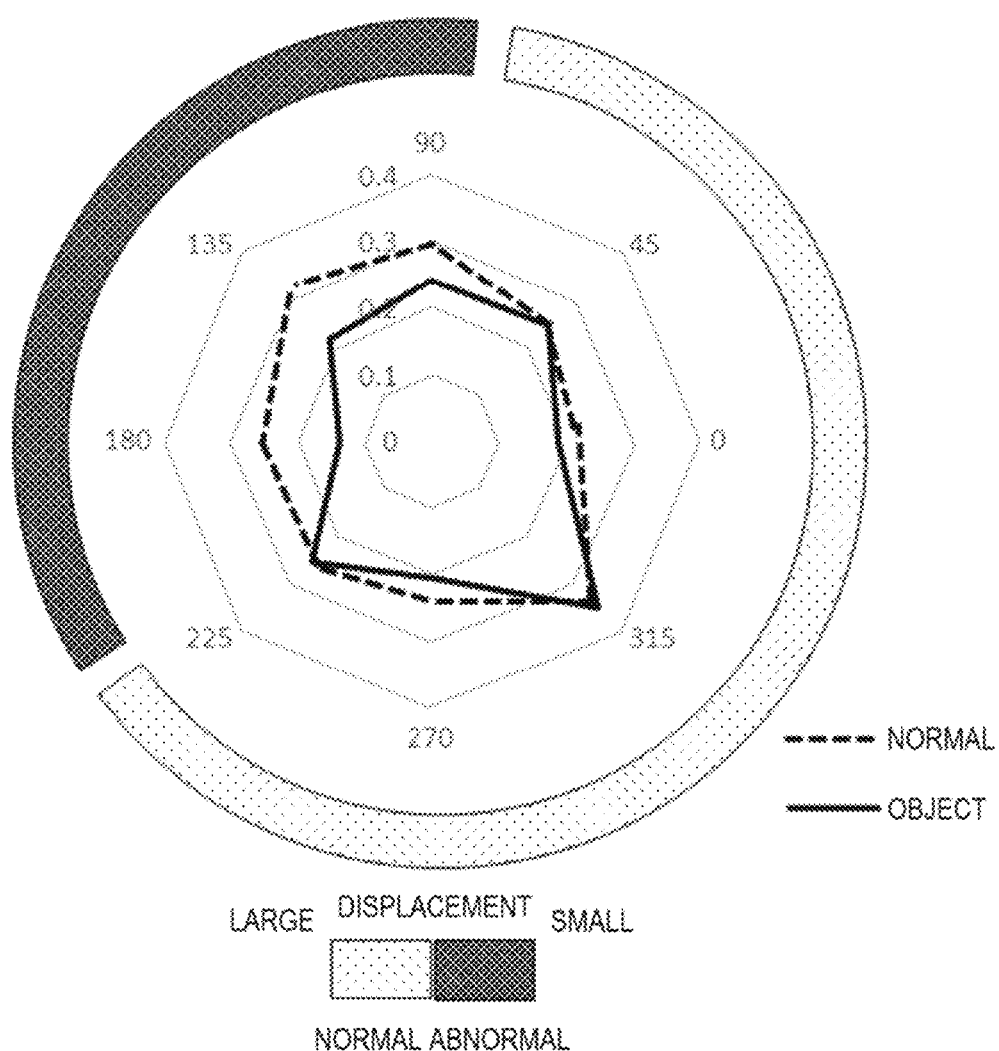

[FIG. 17]
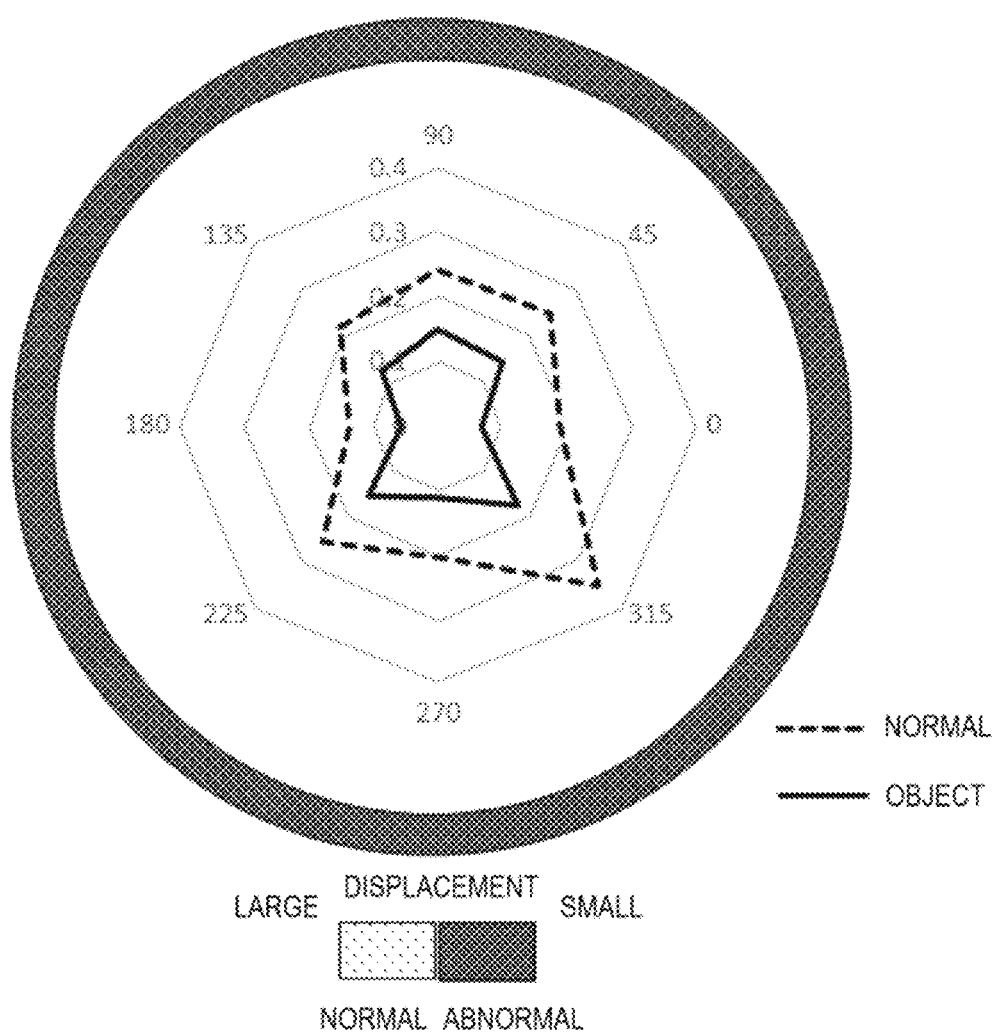

ULTRASONIC IMAGING DEVICE AND ULTRASONIC SIGNAL PROCESSING DEVICE

TECHNICAL FIELD

The present invention relates to a method of processing an ultrasonic reception signal, and relates to a technique for measuring a movement of a tissue or the like in a living body for each type of the tissue and each occurrence factor of the movement.

BACKGROUND ART

Medical image display devices typified by ultrasonic imaging device, magnetic resonance imaging (MRI) device, and X-ray computed tomography (CT) device have been widely used as devices that present, in a form of values or images, information in a living body that cannot be visually confirmed. Particularly, the ultrasonic imaging device is provided with a high temporal resolution as compared to the other image display devices, and can image a beating heart without blurring. In addition, the ultrasonic imaging device not only images morphological information of the tissue in the living body but also can measure tissue properties using the high temporal resolution. For example, the ultrasonic imaging device can measure a blood flow velocity and a modulus of elasticity of the tissue, and contributes to improving a diagnostic accuracy of a doctor by providing the qualitative information to the doctor.

Further, in recent years, a technique for collecting data with a temporal resolution of 1 kHz to 10 kHz while reducing a number of times of ultrasonic transmission has attracted attention, and development of a clinical test function using this technology has also been advanced. The improvement of the temporal resolution works advantageously in that a velocity range can be expanded and an accuracy can be improved in measurement of a tissue movement and blood flow measurement of a subject. For example, a technique described in Non-PTL 1 is a method for measuring a movement of a reflector floating in a liquid using an ultrasonic signal obtained by high-speed transmission and reception, so that a blood flow in a heart is visualized.

Meanwhile, in a technique described in PTL 1, by setting a plurality of measurement points in an ultrasonic image along a myocardial wall from an apex of the heart to an annulus and tracking movement of the measurement points on a plurality of time-series ultrasonic images, the movement of the measurement points associated with a heartbeat is tracked.

In addition, Non-PTL 2 discloses a technique of transmitting and receiving an ultrasonic wave that is a plane wave from a plurality of directions to and from the subject and determining a frequency shifted due to a Doppler effect for each of the plurality of directions so as to obtain a blood flow vector of each point in a subject with the high temporal resolution and to visualize the blood flow vector. From this video, a flow speeding up at a stenosis portion of a blood vessel or a vortex generated downstream thereof can be visually confirmed. The technique described in Non-PTL 2 is different from the technique of Non-PTL 1 and PTL 1 in that a vector field is formed for each combination of transmission and reception angles, thereby providing a stable vector field generation method with less variation.

PTL 2 discloses a technique for estimating strain in a living body by capturing two or more frames of ultrasonic images while applying pressure to the living body through external compression or the like and determining a displacement within the subject through autocorrelation calculation between the frames. In addition, PTL 3 discloses a technique for estimating a modulus of elasticity of a living body by generating a shear wave in the living body, transmitting and receiving the ultrasonic waves in two different directions, and measuring a propagating shear wave velocity.

In the related art, in an ultrasonic imaging device, when measuring a blood flow velocity based on a frequency shifted due to the Doppler effect, reception signals are separated depending on a frequency band region in order to separate a velocity due to tissue movement and a blood flow velocity. Specifically, among Doppler-shifted frequencies determined by performing autocorrelation calculation on two reception signals with different reception time points, a frequency shifted due to tissue movement appears in a low frequency band region and a frequency shifted due to blood flow appears in a high frequency band region. Accordingly, by processing with a filter having an effect of removing the low frequency band region, only a shift frequency component due to the blood flow is extracted.

However, when the blood flow is slow, since shift frequency band regions of the tissue movement and the slow blood flow overlap each other, the shift frequency component due to the blood flow cannot be extracted with the method. Accordingly, Non-PTL 3 discloses a method for separating a blood flow signal included in the shift frequency using an eigenvalue.

CITATION LIST

Patent Literature

PTL 1: Japanese Patent No. 5753798
PTL 2: Japanese Patent No. 5411699
PTL 3: JP-A-2013-544615

Non-Patent Literature

Non-PTL 1: J. Voorneveld, A. Muralidharan, T. Hope, H. J. Vos, P. Kruizinga, A. F. W. van der Steen, F. J. H. Gijsen, S. Kenjeres, N. de Jong, and J. G. Bosch: IEEE Trans. Ultrason. Ferro. Freq. Contl., Vol. 65, No. 12 (2018)
Non-PTL 2: B. Y. S. Yiu, S. S. M. Lai, and A. C. H. Yu: Ultrasound in Med. & Biol., vol. 40, No. 9 (2014)
Non-PTL 3: A. C. H. Yu, and L. Lovstakken: IEEE Trans. Ultrason. Ferro. Freq. Contl., Vol. 57, No. 5 (2010)

SUMMARY OF INVENTION

Technical Problem

As described above, information obtained by using the ultrasonic imaging device is diverse, and includes not only the morphological information but also qualitative information such as the blood flow vector and the modulus of elasticity. However, in order to obtain the plurality of pieces of information, an operator must operate the imaging device for each piece of information to perform ultrasonic imaging using different methods, which costs time and is poor in inspection efficiency. For example, when measuring the displacement in the subject by propagating the shear wave in the living body, as in PTL 3, two or more frames of ultrasonic images are captured, and the displacement within the subject is determined through cross-correlation calculation between the frames, whereas in order to measure the blood flow vector, as in Non-Patent Literatures 2 and 3, it is necessary to determine a Doppler frequency of the ultrasonic reception signal. In the measurement of the blood flow vector, in order to improve the temporal resolution, as in the method of Non-PTL 3, it is necessary to limit a space range to be measured, and it is difficult to measure surrounding information other than the blood flow.

In addition, when a plurality of times of the measurement are performed and the plurality of types of information are obtained, since body movement of the subject also occurs between different times of measurement, the plurality of pieces of information cannot be obtained at the same timing for the same cross section in an inspection object, which hinders comparison of the information.

An object of the invention is to obtain and provide one or more types of information desired by an operator with a high efficiency.

Solution to Problem

In order to achieve the above purpose, an ultrasonic imaging device of the invention includes: a movement vector distribution calculation unit configured to receive a reception signal from a probe that transmits an ultrasonic wave to a subject and receives an ultrasonic wave coming from the subject due to the transmission, and process the reception signal, so as to calculate movement vectors each indicating a movement amount and a movement direction and determine a movement vector distribution for a plurality of points set at least two-dimensionally within a predetermined imaging range in the subject; and a separation filter configured to extract a distribution of one or more desired movement vector components from the movement vector distribution.

Advantageous Effect

According to the invention, a distribution of movement vectors of points set two-dimensionally in a subject can be determined, one or more types of vector components can be distinguished and extracted from the movement vector distribution, and information indicated by the vector components can be displayed.

BRIEF DESCRIPTION OF DRAWINGS

FIG. 1 is a block diagram showing a configuration of an ultrasonic imaging device according to a first embodiment of the invention.

FIG. 2 is an explanatory diagram of a flow of extraction of a vector component from measurement of a movement vector distribution in the ultrasonic imaging device according to the first embodiment.

FIG. 3 is a table showing features of the movement vectors in a subject.

FIG. 4 is a flowchart showing an operation of the ultrasonic imaging device according to the first embodiment.

FIG. 7 is a flowchart showing an operation of a signal processing unit of the ultrasonic imaging device according to the first embodiment.

FIG. 8 shows an example of a sequence when separating transmission and reception for tissue and blood flow measurement and transmission and reception for shear wave measurement in the ultrasonic imaging device according to the first embodiment.

FIGS. 10A to 10D are explanatory diagrams showing an example of a flow of analysis from extraction of particle movement vectors of a shear wave according to the second embodiment.

FIGS. 14A to 14C are explanatory diagrams of measurement of movement vectors of a blood vessel wall and a measurement result thereof according to a third embodiment.

FIG. 16 is an image example of an analysis result obtained by moving body measurement of the blood vessel wall according to the third embodiment.

FIG. 17 is an image example of an analysis result obtained by moving body measurement of the blood vessel wall according to the third embodiment.

DESCRIPTION OF EMBODIMENTS

Figure 5A:
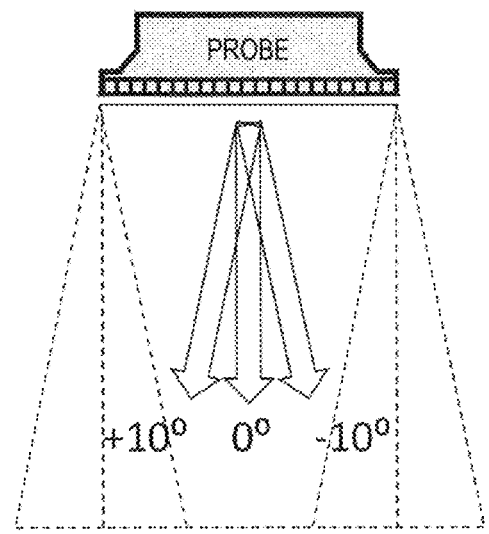
FIG. 5A is an explanatory diagram showing a transmission direction.

An ultrasonic imaging device according to embodiments of the invention will be described using the drawings.

First Embodiment

<Overview of Ultrasonic Imaging Device of First Embodiment>

First, an overview of an ultrasonic imaging device according to a first embodiment will be described with reference to FIG. 1 for showing a device configuration and FIG. 2 for showing a flow of processing.

An ultrasonic imaging device 100 of the present embodiment includes, as shown in FIG. 1, a transmission and reception beam former 30 and a signal processing unit 40. In the signal processing unit 40, at least a movement vector distribution calculation unit 403 and a separation filter 44 are arranged.

The transmission and reception beam former 30 generates and transmits a transmission signal to a probe 20 connected to the transmission and reception beam former 30, and causes the probe to transmit an ultrasonic wave into a subject 10. The ultrasonic wave coming from the subject 20 due to the transmission is received and converted into a reception signal by the probe 20. The transmission and reception beam former 30 receives the reception signal and performs a reception beam forming processing of focusing on a reception focus on a predetermined reception scan line (step S200 in FIG. 2).

The movement vector distribution calculation unit 403 of the signal processing unit 40 calculates movement vectors each indicating a movement amount and a movement direction and determines a movement vector distribution 202 using the reception signal after the reception beam forming processing for a plurality of points set at least two-dimensionally within a predetermined imaging range in the subject (step S201). For example, as will be described later, a movement amount measurement unit 402 of the signal processing unit 40 calculates the movement amounts by detecting a frequency shifted due to an Doppler effect of the reception signal, and the movement vector distribution calculation unit 403 can determine the movement vectors by synthesizing the movement amounts for each combination of transmission and reception directions of the ultrasonic wave to and from the subject 10.

The movement vector distribution 202 includes all movement information of a tissue (including the blood flow) at a position where a plurality of points are arranged, regardless of an occurrence factor thereof. The occurrence factors of the movement include: a blood flow when the position of the point is within the blood vessel; body movement, breathing, heartbeat, and peristaltic movement of a digestive organ for both the blood vessel and an outside of the blood vessel; and a displacement due to an elastic wave when the elastic wave propagates through the subject. All of these pieces of movement information are synthesized and included in the movement vectors.

The separation filter 44 extracts a distribution of one or more desired movement vector components from the movement vector distribution (steps S203a to 203c). That is, the separation filter 44 extracts a distribution of one or more movement vector components among a movement vector component indicating movement of one or more desired tissues among a plurality of tissues constituting the subject 10 and movement vector components indicating movement of the tissue of the subject due to one or more desired movement occurrence factors among the plurality of movement occurrence factors. For example, the plurality of tissues include the blood flow and tissues other than the blood flow, and the movement occurrence factors include the beat, the breathing, and the elastic wave that propagates through the subject.

Specifically, the separation filter 44 can extract, from one movement vector distribution 202, a movement vector component distribution (tissue vector distribution) 204a indicating the movement of the tissue due to the breathing or the beat, a blood flow vector distribution 204b, and an elastic wave vector distribution 204c indicating the movement of the tissue due to the elastic wave.

The separation filter 44 extracts the movement vector component based on one or more among a movement velocity of the tissue indicated by the movement vector (movement amount per unit time), and a frequency and an eigenvalue of the temporal change of the movement vector. In addition, the separation filter 44 extracts a desired movement vector component by determining whether to extract the movement vectors at a corresponding position according to a luminance of a B-mode image generated from the reception signal.

For example, as shown in the table of FIG. 3, the movement vectors of the tissues other than the blood flow, the blood flow, and the elastic wave have differences in the movement velocity (movement amount per unit time), the temporal change frequency and the eigenvalue of the movement vector, and the luminance of the B-mode image, and therefore, in accordance with these differences, the separation filter 44 can extract the desired movement vector component by performing the extraction.

Specifically, regarding the movement velocity of the tissue, the tissue movement due to the heartbeat and the peristaltic movement of the digestive organ is 1-10 mm/s, whereas the blood flow has a wide range of 1-1000 mm/s, and especially has a wide range of a high speed region. For example, a blood flow velocity in arteries and veins is generally about 10 mm/s, whereas a blood flow in the heart may reach 100 mm/s to 1000 mm/s. On the other hand, a velocity of the elastic wave (particle velocity) is about 0.1-10 mm/s.

Next, regarding the temporal change (temporal variation) frequency of a magnitude of the movement vector (movement amount), in the case of the tissue movement or arterial blood, the temporal variation depends on the heartbeat, so the frequency band region is about several Hz. In the case of the blood flow such as venous blood whose magnitude of the movement vector has a small temporal variation, even the blood flow may have a band region in a high frequency region. On the other hand, the temporal variation of the movement vector of the elastic wave (particle velocity) has a high band region of about 100 Hz to 1000 Hz depending on an elastic characteristic of the living body tissue.

On the other hand, in the tissue and the blood flow, constituent elements of the tissue have a size of a few centimeters as a continuum, whereas the blood flow is a liquid in which blood cells and the like are dispersed, and therefore, there is a difference in a spatial structure and a difference occurs in the eigenvalue of the temporal variation of the movement vector. That is, compared to the blood flow, the movement vector of the tissue has very little variation, and therefore, the eigenvalue of the temporal variation of the tissue movement has a component at a low rank (low-order) compared to the blood flow which has a large variation.

It is known that the luminance of the B-mode image is basically lower in the blood vessel, in a gallbladder, in a cyst, and the like than in a substantial part of the tissue. In addition, since the elastic wave (particle velocity) propagates through the tissue as a medium, characteristics in the B-mode image are the same as that of the tissue.

Further, since the elastic wave (particle velocity) generated by using an acoustic radiation pressure is a wave of about one pulse, the elastic wave has transient and non-lasting characteristics. Such characteristics cannot be seen in the tissue movement or the blood flow.

Accordingly, the separation filter 44 can extract the distributions 204a to 204c of the desired movement vector components by performing the extraction using one or more among the movement velocity, the frequency and the eigenvalue of the temporal change of the movement vector, and the luminance of the B-mode image.

The separation filter 44 can cause a display unit 60 to display the extracted distributions (images) 204a to 204c of the one or more movement vector components, for example, in a manner arranged as shown in a screen 210 (FIG. 2).

In this way, according to the ultrasonic imaging device of the present embodiment, the distribution of the movement vectors of the points set two-dimensionally in the subject can be determined, and simultaneously one or more types of the vector components can be extracted from the movement vector distribution to display information indicated by the vector components. When extracting the distributions (images) 204a to 204c of the plurality of movement vector component, the distributions are information obtained at the same timing for the same cross section (imaging range), and thus can be easily compared.

In addition, as shown in FIG. 2, a tissue movement information due to peristalsis and beat 205a, a microvessel distribution information 205b, and a shear wave propagation and particle velocity vector distribution information 205c can be obtained from the one or more extracted distributions (images) 204a to 204c of the movement vector components. Based on these pieces of information, evaluation indexes such as a strain 206a, a blood vessel density 206b, a viscosity/elasticity/structural homogeneity 206c and the like can be calculated. Further, diagnosis information for assisting determination of a fibrosis degree 207a, an inflammation presence/absence of 207b, and fibrosis/fatification degrees 207c can also be provided.

<Detailed Description of Ultrasonic Imaging Device>

Hereinafter, the ultrasonic imaging device according to the first embodiment will be described in more detail.

As described above, the ultrasonic imaging device 100 in FIG. 1 includes the transmission and reception beam former 30 and the signal processing unit 40.

In the signal processing unit 40, an image construction unit 401, a movement amount measurement unit 402, and a data analysis unit 48 are arranged in addition to the above-described movement vector distribution calculation unit 403 and the separation filter 44.

The separation filter 44 includes a velocity, frequency and eigenvalue based separation filter (A) 45, a luminance based separation filter (B) 46, and a vector extraction unit (A×B) 47.

An external input device 70 and a memory 50 are connected to the signal processing unit 40. The external input device 70 receives a selection of a type of the movement vector component (information) to be extracted by the separation filter 44 and the like from an operator. The memory 50 stores the reception signal, the calculated movement vector distribution 202, the extracted distributions 204a to 204c of the movement vector components, and the like as necessary.

<Operation of Each Unit>

An operation (processing) of each unit of the ultrasonic imaging device according to the present embodiment will be described later using a flow of FIG. 4.

Each unit in the signal processing unit 40 can be implemented by software, and a part or all of the units can be implemented by hardware. When implemented by software, the signal processing unit 40 is configured with a processor such as a central processing unit (CPU) or a graphics processing unit (GPU) and a memory, and the functions of the image construction unit 401, the movement amount measurement unit 402, the movement vector distribution calculation unit 403, the separation filter 44, and the data analysis unit 48 are implemented by reading and executing a program stored in advance in the memory. In addition, when implemented by hardware, a custom IC such as an application specific integrated circuit (ASIC) and a programmable IC such as a field-programmable gate array (FPGA) may be used to perform a circuit design such that at least the operations of the image construction unit 401, the movement amount measurement unit 402, the movement vector distribution calculation unit 403, the separation filter 44, and the data analysis unit 48 are implemented.

The transmission and reception beam former 30 has functions of transmission control for applying a voltage corresponding to a desired transmission waveform to the probe and reception control for receiving an electrical signal converted from a reflected wave from an object.

With these functions, the transmission and reception beam former 30 generates and transmits the transmission waveform to the probe 20 which is connected to the transmission and reception beam former 30, and transmits the ultrasonic wave from the probe 20 into the subject 10 (step S20 in FIG. 4). The ultrasonic wave, such as the reflected wave coming from the subject 20 due to the transmission is received by the probe 20 and converted into the reception signal. The transmission and reception beam former 30 receives the reception signal and performs the reception beam forming processing of focusing on the reception focus on the predetermined reception scan line, and converts the reception signal into two-dimensional data in which a complex RF signal (line data) is aligned in an azimuth direction (reception scanning line direction) (step S21).

The transmission and reception in steps S20 and S21 will be described in more detail.

Figure 5B:
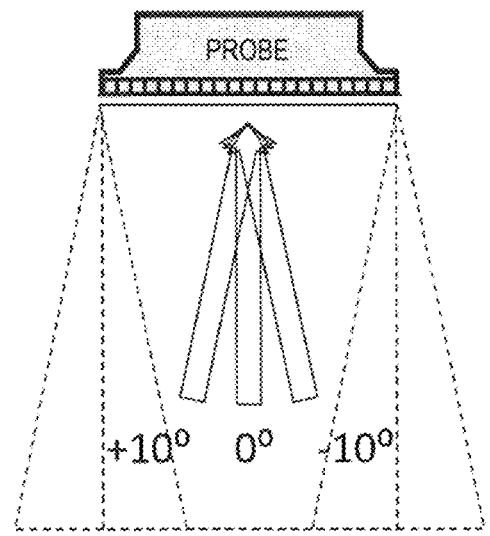
FIG. 5B is an explanatory diagram showing a reception direction of an ultrasonic wave of the ultrasonic imaging device according to the first embodiment.
Figure 6A:
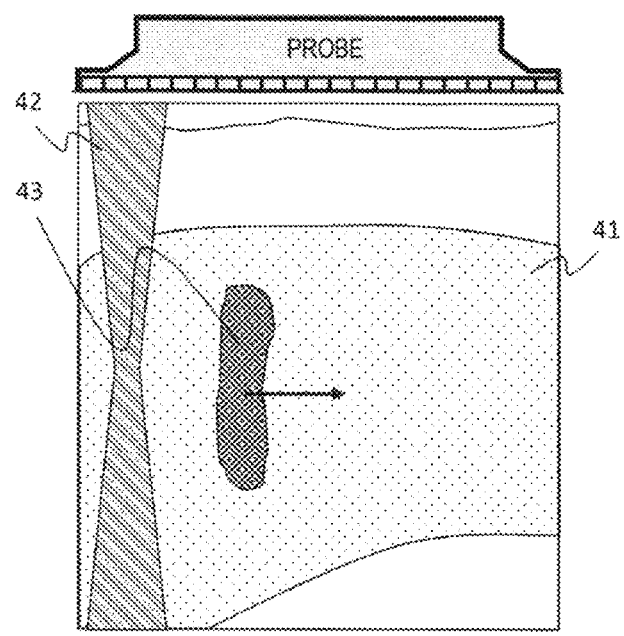
FIG. 6A is an explanatory diagram showing transmitting a focused ultrasonic wave to an object for shear wave excitation of the ultrasonic imaging device.

First, the ultrasonic wave is transmitted from the probe 20 in directions specified in advance. For example, as shown in FIG. 5(*a*), the transmission is performed in three directions [−10, 0, +10] (unit: degree). The ultrasonic wave to be transmitted is preferably a plane wave as shown in FIG. 6(*b*). Further, the reflected wave or the like from the inside of the subject 10 is received by each electro-acoustic transducer element constituting the probe 20 for each transmission. The transmission and reception beam former 30 sets a plurality of parallel reception scan lines for each of the three directions [−10, 0, +10] (unit: degree) as shown in FIG. 5(*b*), and performs the reception beam forming for each reception scan line to obtain a reception RF signal for each scan line. That is, nine combinations of transmission and reception are present, which is obtained by 3×3. Since the movement vector measurement is performed in pairs of transmission and reception, nine pairs obtained by 3×3 are established in the example of FIG. 5. A direction of the movement vector calculated in each pair basically follows the reception direction. That is, the movement vector in the reception scanning line direction is calculated. Since the movement vector calculated for each pair is a component vector, finally, the movement vectors are geometrically integrated (synthesized) to be a result of the movement vector of the reception focus.

When transmitting the plane wave, by controlling a delay amount of the transmission signal input to each of the electro-acoustic transducer elements provided in an array shape inside the probe 20, the plane waves in the three directions [−10, 0, +10] (unit: degree) can be transmitted. In the case of the plane wave transmission, since a space region that can be covered by one transmission is wide, time required for signal acquisition from the entire object can be reduced as compared with a focus transmission in which a desired range is covered by moving a transmission location. For example, when all signals are acquired in one transmission from a range where a sound velocity of the object is 1500 m/s and a depth is 7.5 cm (a horizontal width is a caliber of the probe), the transmission and reception is completed in 0.1 msec (10 kHz).

In the present embodiment, such multidirectional transmission and reception of the ultrasonic wave is performed at least twice.

Next, the movement amount measurement unit 402 calculates a movement amount of each point (pixel) set vertically and horizontally in an imaging region by using the nine pieces of two-dimensional data acquired at least twice in a time series. The points are moving bodies, and are set at least two-dimensionally for living body tissues such as the blood vessel and the organ, and the blood flow in the blood vessel. The points (moving body) move due to particle movement associated with the blood flow, the breathing, the heartbeat, and the peristaltic movement of the digestive organ, and the propagation of shear wave (biological tissue from a micro viewpoint).

The movement amount measurement unit 402 performs autocorrelation calculation between the reception RF signals acquired at least twice in the time series with the same combination of transmission and reception directions. Accordingly, the frequency shifted due to the Doppler effect is calculated. Based on the shifted frequency, the movement velocity of the point on the reception scan line in the reception scanning line is calculated with a known method. The movement amount (per unit time) of the point is determined based on the calculated movement velocity and a time interval of the twice transmission. The movement direction is the direction of the reception scanning line. Accordingly, the movement vector of each point is determined.

The movement vector distribution calculation unit 403 determines the movement vector in the scan line direction of each point by performing the calculation for each of the nine combinations of the transmission and reception. Further, the movement vector distribution 202 is calculated by synthesizing the movement vector of the same point (step S23).

Regarding the measurement method of the movement vector, in addition to the autocorrelation method using the RF signal described in the present embodiment, in general, a method using luminance information after performing an envelope detection and a pattern matching method using two-dimensional information in an azimuth direction and a depth direction are known. The present embodiment relates to a function and a device including moving body analysis using the calculation result of the movement vector as input information. Regarding the calculation method of the movement vector, the method is not particularly limited, and any calculation method may be used.

The separation filter (A) 45 extracts the component included in the movement vector distribution 202 using the velocity of the movement vector, the frequency and the eigenvalue of the temporal change of the movement vector. Herein, the separation filter (A) 45 separates the tissues excluding the blood flow and the blood flow by using the frequency of the temporal change of the movement vector and an identity with surrounding pixels (step S28). The processing evaluates both a temporal identity and a spatial identity, and in general, the blood flow component is low in both temporal and spatial identity (a rank of the eigenvalue is high). The component of the elastic wave (particle velocity) is similar in the temporal and spatial identities to the blood flow, and is mixed in the blood flow component as an action of the separation filter (A) 45. However, since the propagation of the elastic wave is a transient phenomenon unlike the blood flow and the tissue, the temporal identity increases as observation time increases.

On the other hand, in order to further improve a extraction accuracy of the blood flow or the elastic wave (particle velocity) using the B-mode image, the image construction unit 401 reconstructs the B-mode image using the reception RF signal obtained when the transmission angle of the ultrasonic wave is 0 degree (step S24). The luminance separation filter (B) 46 performs luminance analysis of the B-mode image to extract a high luminance region or a low luminance region (step S25).

The vector extraction unit (A×B) 47 multiplies the extraction result of the separation filter (A) 45 and the extraction result of the luminance separation filter (B) 46 to improve an extraction accuracy of the desired vector component (blood flow, elastic wave, tissue movement).

Herein, a processing method in which the separation filter (A) 45 and the like respectively extract the tissue movement, the blood flow, and the elastic wave (particle velocity) after step S28 will be further described with reference to FIG. 7. First, separation of the elastic wave (particle velocity) will be described. As already described with reference to FIG. 3, the characteristics of the elastic wave (particle velocity) include a high frequency and unstable time and space. Therefore, the separation filter (A) 45 analyzes the temporal variation of an amplitude value (magnitude) of the movement vector of each point, and extracts the vector component of the elastic wave (particle velocity) from the movement vector by extracting an upper band region from the vicinity of 100 Hz. In addition, when the observation time is adjusted to the propagation time of the elastic wave (less than 1 second), the extraction accuracy can be further increased by using the instability in the time and space of the elastic wave (particle velocity) and extracting a high-rank component of the eigenvalue of the temporal variation of the amplitude value (magnitude) of the movement vector.

On the other hand, the luminance separation filter (B) 46 performs the luminance analysis of the B-mode image to extract the high luminance region (step S25-2).

The vector extraction unit (A×B) 47 multiplies the extraction result of the separation filter (A) 45 and the extraction result of the luminance separation filter (B) 46 to accurately extract the distribution 204c of the elastic wave (particle velocity).

By separating the region satisfying the above conditions, the vector component related to the elastic wave (particle velocity) can be selectively obtained.

Next, a method for separating the vector related to the blood flow will be described. The characteristics of the blood flow include a high rank of the eigenvalue and a low B-mode image luminance. Regarding the frequency, a low frequency removing filter in a range basically not reaching 100 Hz is effective, but the effect is limited in the low-speed blood flow. In other words, since the frequency band region to be separated changes depending on whether the region of interest is high speed or low speed, it is necessary to adjust according to judgement of an operator. Therefore, basically, the separation filter (A) 45 extracts the point of the high rank eigenvalue component from the movement vector distribution (step S28-3). In addition, the luminance separation filter (B) 46 extracts the low luminance region from the B-mode image (step S25-3). The vector extraction unit (A×B) 47 multiplies the extraction result of the separation filter (A) 45 and the extraction result of the luminance separation filter (B) 46 to extract the distribution 204c of the blood flow vector. However, when a target blood vessel is very thin and a difference from the tissue cannot be obtained with the spatial resolution of the B-mode image, the separation filter (B) is not necessarily required to act.

When it is desired to specifically extract a blood flow vector in a specific flow velocity range, it can be implemented by adding a band region limitation to the frequency information in step S28-3.

Finally, a method for extracting a tissue movement vector will be described. Since characteristics of the tissue movement include a low frequency, a low-rank eigenvalue component, and a high luminance of the B image, a vector satisfying these conditions may be selected. That is, the separation filter (A) 45 extracts the point of the low rank eigenvalue with the low frequency from the movement vector distribution (step S28-4). In addition, the luminance separation filter (B) 46 extracts the high luminance region from the B-mode image (step S25-2). The vector extraction unit (A×B) 47 multiplies the extraction result of the separation filter (A) 45 and the extraction result of the luminance separation filter (B) 46 to extract the distribution 204c of the tissue movement vector.

The tissue movement varies in the features depending on a type and a location of the tissue of interest as compared to the elastic wave (particle velocity) and the blood flow. Therefore, a method of subtracting the information of the blood flow and the particle velocity from the entire information of the vector distribution is also effective.

The data analysis unit 48 calculates, based on the result of the vector calculation, information 205a to 205c, evaluation indexes 206a to 206c, and diagnosis information 207a to 207c which are useful for medical determination such as a state and a property of the object (the subject 10) (step S27).

The separation filter 44 displays the movement vector component distributions 204a to 204c extracted as described above on the display unit 60 as shown in the screen 210 (see FIG. 2) (step S29). In addition, the data analysis unit 48 displays the calculated information 205a to 205c, 206a to 206c, and 207a to 207c on the display unit 60.

Figure 6B:
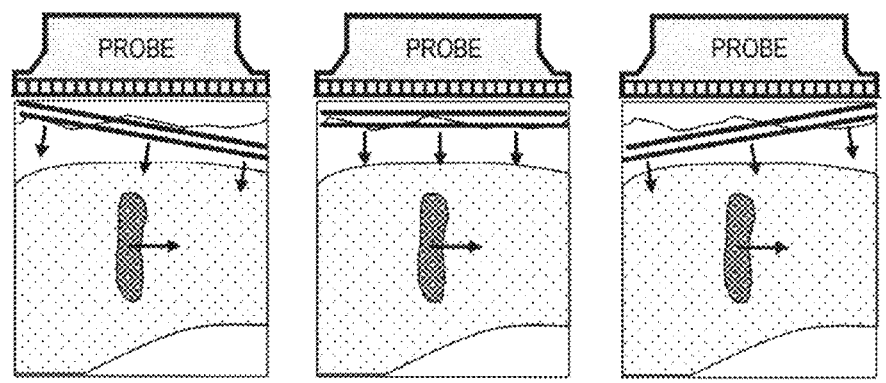
FIG. 6B is an explanatory diagram showing transmitting and receiving an ultrasonic wave while changing a direction when the shear wave propagates through the object according to the first embodiment.

When the elastic wave is measured as in the above-described embodiment, as shown in FIG. 6, after transmitting a focused ultrasonic wave 42 for exciting the shear wave 43 to the object 41 (liver in FIG. 6) 41 of the subject 10, the transmission for vector measurement is continuously performed while the shear wave (elastic wave) 43 propagates through the object 41 as shown in FIG. 6(b).

In addition, when measuring the shear wave (elastic wave), the transmission and reception for the tissue and blood flow measurement is performed while propagating the shear wave as in the embodiment described above. However, as shown in FIG. 8, before a burst wave transmission, the tissue and the blood flow measurement may be performed to eliminate an influence of a tissue displacement due to the shear wave, and the elastic wave (shear wave) may be measured after the burst wave transmission.

Second Embodiment

Figure 9A:
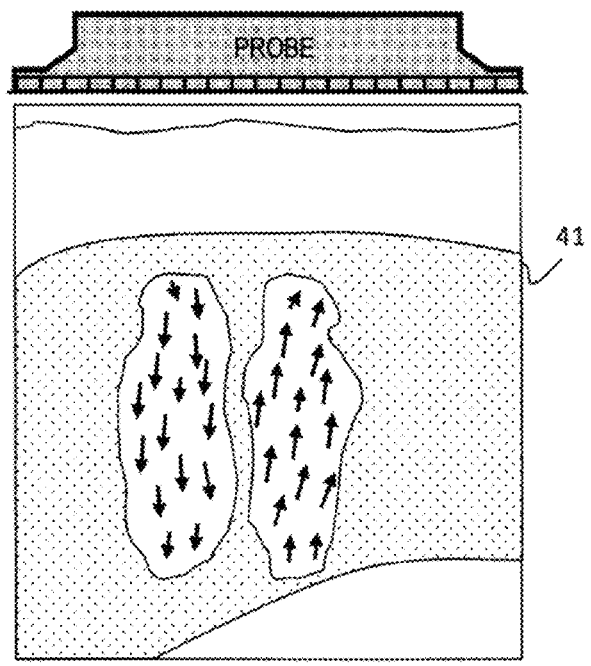
FIG. 9A is an image example showing particle movement vectors of a shear wave of a normal subject.
Figure 9B:
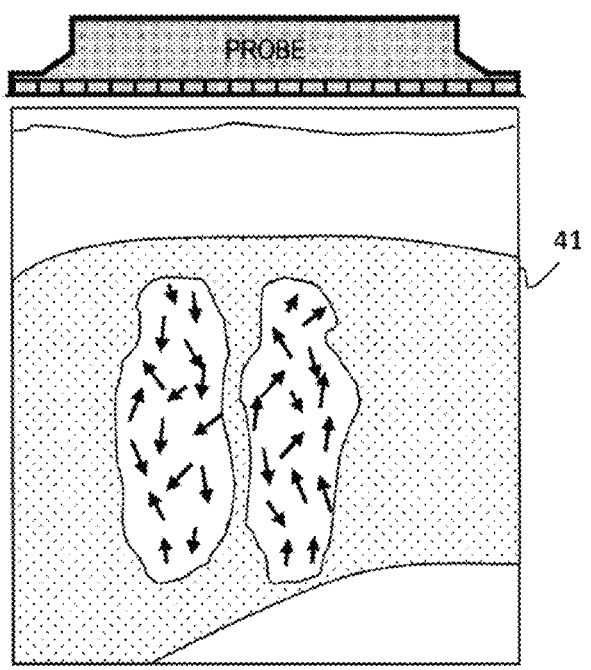
FIG. 9B is an image example showing particle movement vectors of a shear wave of a subject having a disease according to a second embodiment.

As a second embodiment, FIGS. 9(a) and 9(b) indicate display screen examples for displaying the shear wave (elastic wave) vector component distribution extracted in the first embodiment for a normal subject and a disease subject (for example, liver fibrosis). FIG. 9(a) is a diagram indicating a distribution of a shear wave (elastic wave) vector of the normal subject. For a positive pressure (a region of a wave on a right side of the drawing) and a negative pressure (a region of a wave on a left side of the drawing) of the shear wave, each of particle velocities forming the shear wave is displayed as a vector. For the normal subject, an orientation (angle) of the vector is uniform within each region.

FIG. 9(b) is a diagram indicating a distribution of shear wave vectors of the disease subject. For example, when the disease subject is assumed as a fibrotic tissue, since the shear wave is deformed together with propagation, an abnormality can be determined with higher sensitivity by measuring the particle velocity as a component thereof instead of an entire shape of the shear wave and analyzing a non-uniformity of the angle.

FIGS. 10(a) to 10(d) show a flow of an example of a calculation in which the data analysis unit 48 evaluates homogeneity of a direction of the movement vector based on a result of the vector measurement. As shown in FIG. 10(a), the movement vector distribution calculation unit 403 calculates the movement vector distributions of the shear wave and a background. As shown in FIG. 10(b), the separation filter 44 extracts a movement vector in the shear wave region. As shown in FIG. 10(c), the data analysis unit 48 extracts a vector of a region of interest (ROI) in FIG. 10(b) as a matrix, and calculates a variance of the angle of the vector as a diagnosis index as shown in FIG. 10(d).

Figure 11A:
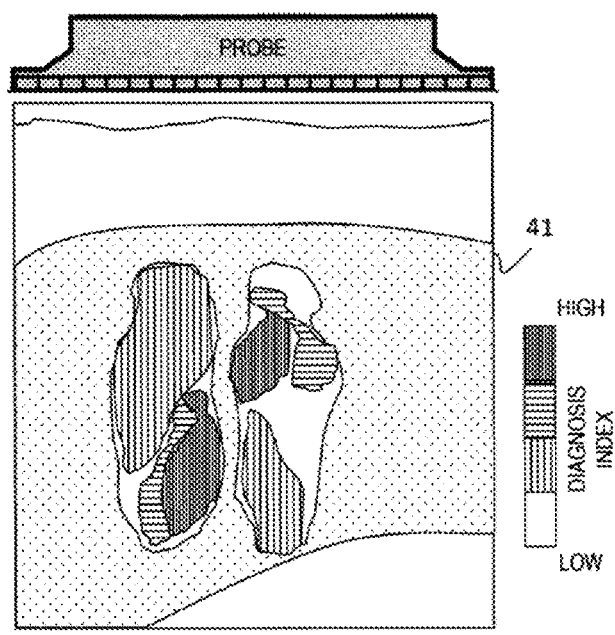
FIGS. 11A to 11C are display image examples of the particle movement vectors of the shear wave according to the second embodiment.
Figure 11B:
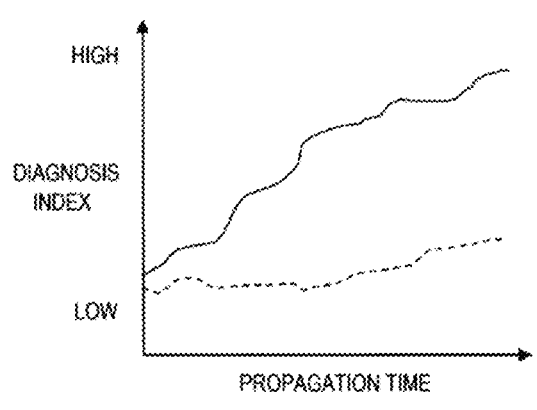
Figure 11C:
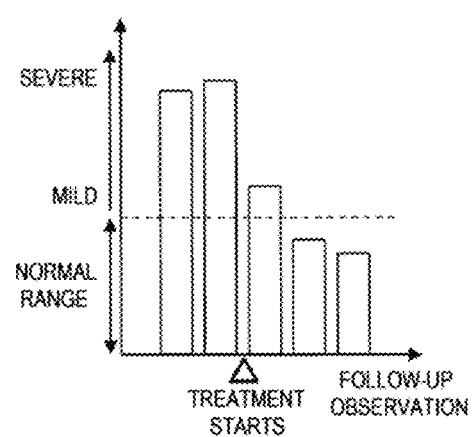

In addition, a statistical value such as a standard deviation can be determined as the diagnosis index. A two-dimensional distribution of the diagnosis index can be formed by providing the region of interest on the entire screen. FIGS. 11(a) to 11(c) show display examples of the distribution of the diagnosis index calculated by the data analysis unit 48. FIG. 11(a) is a display example in which the diagnosis index (variance a for each ROI in FIG. 10(d)) is expressed as a texture in the region of the ROI, and FIG. 11(b) is a graph indicating a transition of the diagnosis index (average value) associated with the propagation of the shear wave. In the diagnosis index shown in FIG. 11(b), when an abnormality is present in the tissue structure, as the propagation time becomes longer, a "disorder of the direction" of the particle velocity becomes obvious and the diagnosis index (direction variance) increases, but a homogeneous medium does not increase. FIG. 11(c) is a graph showing a transition of a diagnosis index (gradient of the direction variance) in a follow-up (follow-up observation). In the graph of FIG. 11(c), a therapeutic effect may be determined by confirming that a numerical value decreases with time.

Figure 12A:
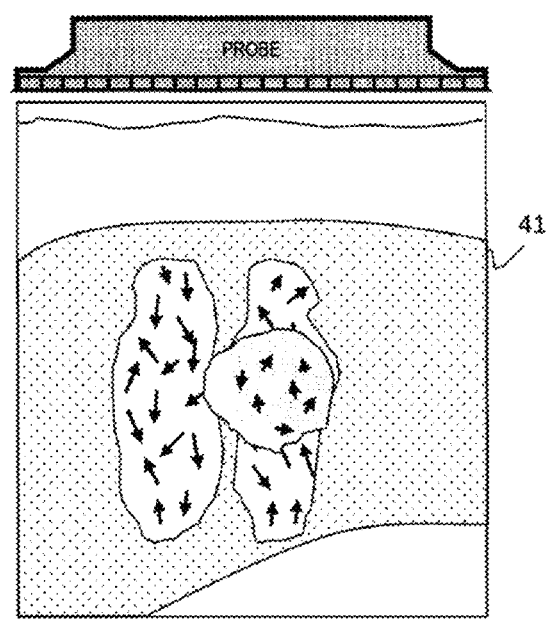
FIG. 12A is a display image example of the particle movement vectors of the shear wave.
Figure 12B:
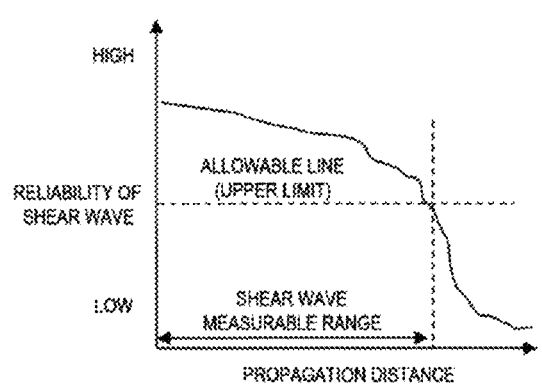
FIGS. 12B and 12C are image examples showing analysis results of a reliability index according to the second embodiment.
Figure 12C:
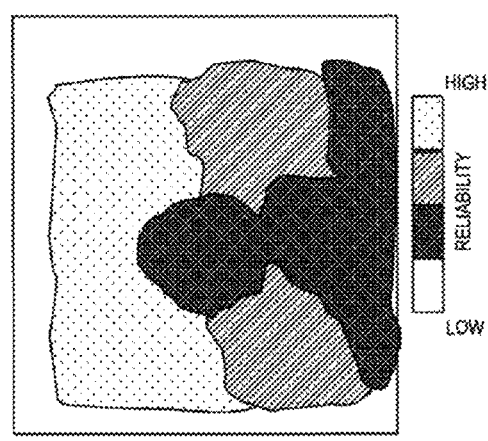

FIGS. 12(a) to 12(c) are examples of the display for evaluating whether the shear wave can be measured or the reliability of measurement result. FIG. 12(a) is a diagram illustrating a vector distribution of the shear wave (elastic waves) extracted by the device of the present embodiment. In a central region, the vector size (magnitude) is reduced. FIG. 12(b) is a graph illustrating a transition in which the numerical value indicating the reliability of the shear wave calculated by the data analysis unit 48 changes as a propagation distance increases. As an example of the numerical value indicating the reliability, a vector angular variance or a vector size can be used. From the graph of FIG. 12(b), it is possible to determine not only the reliability of the shear wave measurement but also in which range of a propagation direction the velocity measurement is performed. FIG. 12(c) is a spatial distribution diagram of a reliability index, in which a vertical axis represents a depth of the subject and a horizontal axis represents the propagation direction of the shear wave.

Figure 13A:
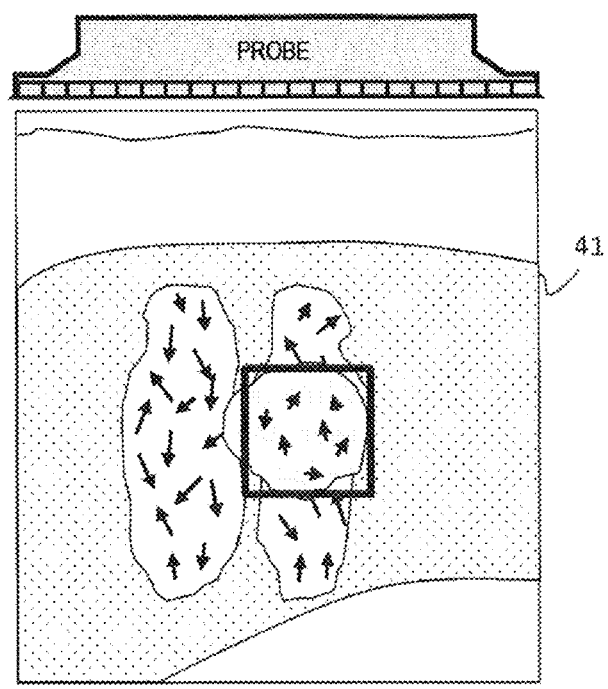
FIG. 13A is a display image example of the particle movement vector of the shear wave.
Figure 13B:
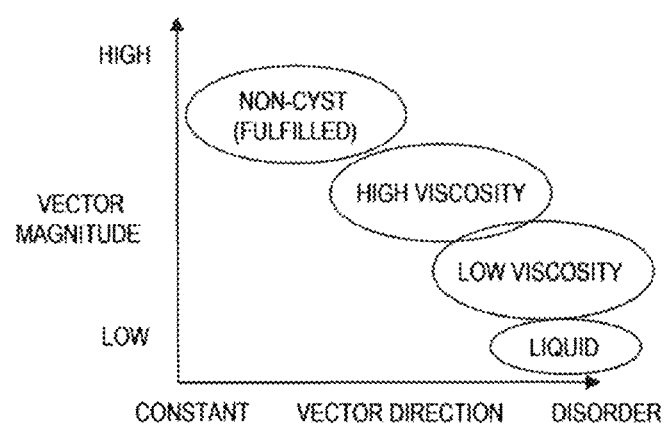
FIG. 13B is an image example showing an analysis result of a cystic lesion according to the second embodiment.

FIGS. 13(a) to 13(b) are diagrams illustrating an example of method for determining a cyst. FIG. 13(a) is an image illustrating the extracted vector of the shear wave, and it can be seen that the vector size (magnitude) decreases in a central region. In the case of a non-cyst, the vector distribution in the central region is a distribution having a certain direction. In a case of a cyst with a high viscosity, a vector distribution includes a disorder of the direction. In a case of a cyst with a low viscosity, the vector distribution is disordered in the direction, and the magnitude of the vector is reduced. On the other hand, in the case of a non-viscous fluid (liquid), the vector distribution is 0, that is, disappears. FIG. 13(b) is an example of a graph classified according to the magnitude and the direction of the vector with respect to a property of an object.

Third Embodiment

As a third embodiment, FIGS. 14(a), 14(b), and 14(c) show a movement vector measurement method for evaluating a property of a blood vessel and a measurement result.

As shown in FIG. 14(a), for the blood vessel, a transmission and reception is performed in a direction specified in advance (herein, a blood vessel cross section). When a number of times of transmission is N, $N^2$ transmission and reception pairs (that is, movement vector measurement results) are established. The movement vector distribution calculation unit 403 calculates the movement vector distribution by synthesizing the movement vector measurement results. On the other hand, as shown in FIG. 14(b), the movement vector of the blood vessel cross section can be extracted by preparing a filter image for extracting a target blood vessel region (region from an inner diameter to an outer diameter) as shown in FIG. 14(c) based on luminance information of a B-mode and multiplying the motion vector distribution. Particularly, in the case of a carotid artery, a luminance tends to be higher than that of a surrounding tissue on a B-mode image, and a configuration of the filter image using the luminance information is a simple and effective method. As shown in FIG. 14(b), in the case of the blood vessel, the magnitude of the vector decreases from the inner diameter to the outer diameter.

As a method for extracting the blood vessel region, in addition to the method using the above-described luminance information, a method using a frequency or an eigenvalue is also effective. In a region classification of FIG. 7, the blood vessel region belongs to the tissue movement. However, when the carotid artery is targeted, an influence of the movement due to the breathing and the peristalsis is very slight unlike an abdominal tissue. Therefore, by configuring a filter for removing, particularly the low frequency region from the low frequency and low rank eigenvalue components, the movement of the blood vessel region associated with the beat can be specifically extracted. In addition, for example, it is also effective to extract a periodic movement synchronized with a heart motion by a frequency analysis using an ECG.

Figure 15A:
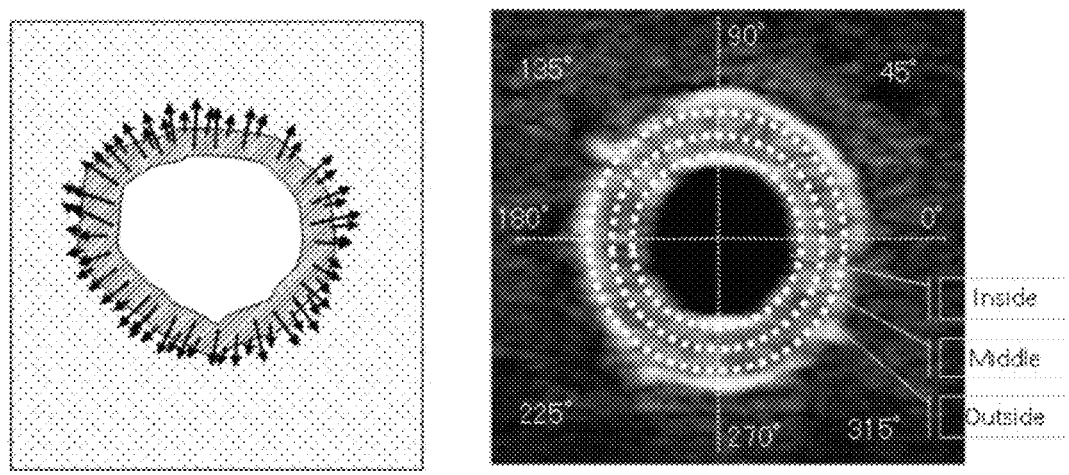
FIGS. 15A and 15B are image examples for displaying a measurement result and an analysis example of the movement vectors of the blood vessel wall according to the third embodiment.
Figure 15B:
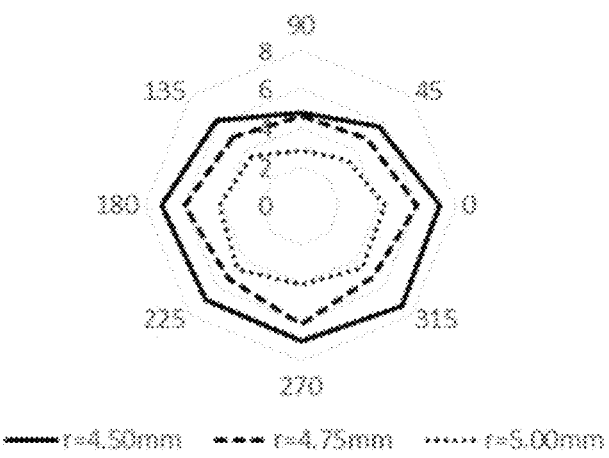

FIGS. 15(a) and 15(b) are diagrams illustrating an example of a displacement measurement result of the blood vessel. A diagram on a left side of FIG. 15(a) shows a movement vector distribution of the blood vessel cross section similar to FIG. 14(b). In a diagram on a right side of FIG. 15(a), a measurement region is set by three circular rings having a radius of, for example, r=4.50 mm, r=4.75 mm, and r=5.00 mm from the inner diameter to the outer diameter of the blood vessel cross section, and the vector information is extracted. FIG. 15(b) is a radar display illustrating a displacement (magnitude of the vector) in the annular rings having a radius of r=4.50 mm, r=4.75 mm, and r=5.00 mm from a position center of the radius in the right side diagram of FIG. 14. An inner diameter side of the blood vessel has a large displacement, and the displacement decreases as approaching an outer diameter side.

FIG. 16 illustrates an example of a display form of the blood vessel property evaluation. Herein, the example is an example of a case of the blood vessel with a plaque. A central graph in the display example of FIG. 16 shows a displacement (magnitude of the movement vector) of the object due to the beat at the predetermined radius of the blood vessel cross section (solid line) by a method similar to FIG. 15(b) and a displacement (magnitude of the movement vector) of a normal blood vessel as a comparative example (broken line). In the example of FIG. 16, it can be seen that in an angle range of 90 degrees to 225 degrees, the displacement of the blood vessel of the object is smaller than the displacement of the normal blood vessel of the comparative example, and the blood vessel becomes hard in the range and cannot be displaced. Therefore, an azimuth of an abnormal region (90 degrees to 225 degrees) is displayed in a dark color by a circular display arranged around such that a fact that the plaque is present can be visually confirmed.

FIG. 17 shows a display form of the blood vessel property evaluation similar to that of FIG. 16, which is a case of an arteriosclerotic blood vessel. It can be seen that the displacement of the blood vessel of the object is smaller than the displacement of the normal blood vessel of the comparative example over an entire circumference of 360 degrees, and the entire blood vessel becomes hard and cannot be displaced. Therefore, an azimuth of an abnormal region (entire circumference) is displayed in the dark color by the circular display arranged around such that a fact that the arteriosclerosis is present can be visually confirmed.

Figure 18A:
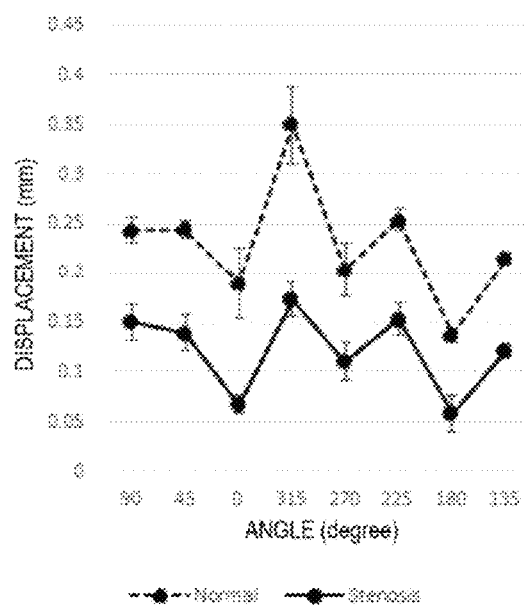
FIGS. 18A and 18B are image examples of an analysis result obtained by moving body measurement of the blood vessel wall according to the third embodiment.
Figure 18B:
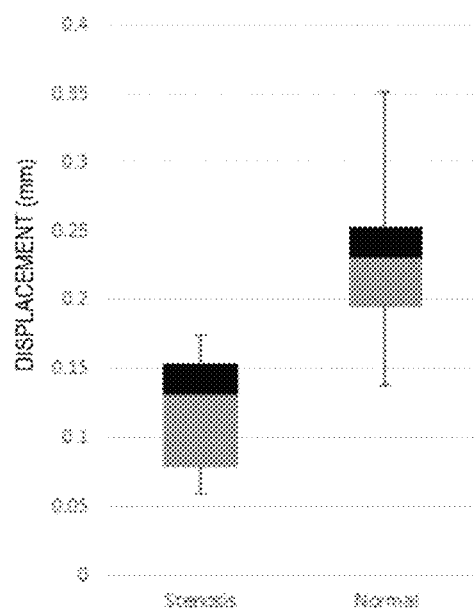

FIG. 18 is an example in which a blood vessel property evaluation result is displayed with a graph. FIG. 18(a) is a graph in which a displacement measurement result for each angle of FIG. 17 is displayed, and FIG. 18(b) is a graph showing a variation of the displacement in all azimuth angles as a difference between the blood vessel having the arteriosclerosis (blood vessel in FIG. 17) and the normal blood vessel of the comparative example. By displaying these graphs, a material for the operator to diagnose the blood vessel having the arteriosclerosis can be provided.

REFERENCE SIGN LIST 10 subject
20 probe
30 transmission and reception beam former
40 signal processing unit
401 image construction unit
402 movement amount measurement unit
403 movement vector distribution calculation unit
44 separation filter
45 velocity, frequency and eigenvalue based separation filter
46 luminance separation filter
47 vector extraction unit
48 data analysis unit

The invention claimed is:

1. An ultrasonic imaging device, comprising:
a movement vector distribution calculation unit configured to receive a reception signal from a probe that transmits an ultrasonic wave to a subject and receives an ultrasonic wave coming from the subject due to the transmission, and process the reception signal, so as to calculate movement vectors each indicating a movement amount and a movement direction and determine a movement vector distribution for a plurality of points set at least two-dimensionally within a predetermined imaging range in the subject; and a separation filter configured to extract a distribution of one or more desired movement vector components from the movement vector distribution;

wherein the separation filter is configured to extract a plurality of types of the distributions of movement vector components from the same movement vector distribution and cause a display unit to simultaneously display the plurality of types of the distributions.

2. The ultrasonic imaging device according to claim 1, wherein the separation filter is configured to extract a distribution of one or more movement vector components among a movement vector component indicating movement of one or more desired tissues among a plurality of tissues constituting the subject and a movement vector components indicating movement of the tissues of the subject due to one or more desired movement occurrence factors among a plurality of movement occurrence factors.

3. The ultrasonic imaging device according to claim 2, wherein the plurality of tissues include a blood flow and a tissue other than the blood flow, and the separation filter is configured to extract, from the movement vector distribution, a distribution of either one of a blood flow vector and a movement vector of the tissue other than the blood flow as the movement vector component.

4. The ultrasonic imaging device according to claim 2, wherein the plurality of movement occurrence factors include a beat, a breathing, and an elastic wave propagating through the subject.

5. The ultrasonic imaging device according to claim 4, wherein the separation filter is configured to extract a distribution of one of the vector components that indicates the movement of the tissue due to the propagation of the elastic wave through the subject.

6. The ultrasonic imaging device according to claim 1, wherein the movement vector distribution calculation unit is configured to calculate the movement amounts by detecting a frequency shifted due to an Doppler effect of the reception signal.

7. The ultrasonic imaging device according to claim 6, wherein the movement vector distribution calculation unit is configured to determine the movement vectors by processing each of reception signals obtained by transmitting the ultrasonic wave to the subject from a plurality of directions, calculating movement amounts for each of the plurality of directions, and combining the calculated movement amounts for each of the plurality of directions.

8. The ultrasonic imaging device according to claim 7, wherein the separation filter is configured to generate an image of the subject based on the reception signals, and extract the movement vectors of the movement vector distribution at a corresponding position based on a luminance of the image.

9. The ultrasonic imaging device according to claim 1, wherein the movement vector distribution calculation unit is configured to calculate the movement vector distribution in a time series, and the separation filter is configured to extract the movement vector component based on a temporal change of the movement vector.

10. The ultrasonic imaging device according to claim 9, wherein the separation filter is configured to extract the movement vector component using any one of a movement velocity indicated by the movement vector, a frequency and an eigenvalue of the temporal change of the movement amount indicated by the movement vector.

11. The ultrasonic imaging device according to claim 1, wherein the separation filter is configured to calculate predetermined evaluation indexes based on the extracted movement vector component distribution and cause a display device to display each of the evaluation indexes.

12. An ultrasonic signal processing device, comprising:

a movement vector distribution calculation unit configured to receive and process a reception signal from a probe that transmits an ultrasonic wave to a subject and receives the reception signal, so as to calculate movement vectors each indicating a movement amount and a movement direction and determine a movement vector distribution for a plurality of points set at least two-dimensionally within a predetermined imaging range in the subject;

a separation filter configured to extract a distribution of one or more desired movement vector components from the movement vector distribution; and a data analysis unit configured to determine a reliability index of the one or more desired movement vector components and cause a display unit to display a spatial distribution of the reliability index.

* * * * *